United States Patent
Seo et al.

(10) Patent No.: US 12,285,219 B2
(45) Date of Patent: Apr. 29, 2025

(54) METHOD AND PROGRAM FOR MODELING PERSONALIZED BREAST IMPLANT

(71) Applicant: SEEANN SOLUTION CO., LTD., Incheon (KR)

(72) Inventors: An Na Seo, Incheon (KR); Jung Dug Yang, Daegu (KR); Dong Hun Choi, Daegu (KR); Young Jin Jeong, Daegu (KR)

(73) Assignee: SEEANN SOLUTION CO., LTD., Incheon (KR)

( * ) Notice: Subject to any disclaimer, the term of this patent is extended or adjusted under 35 U.S.C. 154(b) by 368 days.

(21) Appl. No.: 17/844,577

(22) Filed: Jun. 20, 2022

(65) Prior Publication Data
US 2022/0395329 A1 Dec. 15, 2022

Related U.S. Application Data

(63) Continuation of application No. PCT/KR2020/018592, filed on Dec. 17, 2020.

(30) Foreign Application Priority Data

Dec. 20, 2019 (KR) .................. 10-2019-0171953
Dec. 17, 2020 (KR) .................. 10-2020-0176976

(51) Int. Cl.
*A61B 34/10* (2016.01)
*A61F 2/12* (2006.01)
*G06T 7/33* (2017.01)

(52) U.S. Cl.
CPC ................ *A61B 34/10* (2016.02); *A61F 2/12* (2013.01); *G06T 7/337* (2017.01);
(Continued)

(58) Field of Classification Search
CPC .............. A61B 34/10; A61B 2034/102; A61B 2034/108; A61F 2/12; A61F 2240/00;
(Continued)

(56) References Cited

U.S. PATENT DOCUMENTS 7,058,439 B2 6/2006 Eaton et al.
2009/0067698 A1* 3/2009 Shinagawa ............... G06T 7/11
382/131

(Continued)

FOREIGN PATENT DOCUMENTS

JP 2015-054089 A 3/2015
KR 10-2019-0046465 A 5/2019
KR 10-2019-0134864 A 12/2019

OTHER PUBLICATIONS

Google machine translation of Jin et al., published at 2018 Korean Software Conference Paper Collection, pp. 1267-1269, Dec. 2018.*
(Continued)

*Primary Examiner* — Casey L Kretzer
(74) *Attorney, Agent, or Firm* — Studebaker Brackett PLLC

(57) ABSTRACT

The present disclosure relates to a method for modeling a personalized breast implant including the operations of: obtaining medical image data and body scan data; obtaining first image data by 3D modeling the medical image data; obtaining second image data by 3D modeling the body scan data; creating third image data by merging the first image data and the second image data; and creating breast implant appearance information on the basis of the third image data.

8 Claims, 10 Drawing Sheets

(52) U.S. Cl.
CPC ... *A61B 2034/102* (2016.02); *A61B 2034/108* (2016.02); *A61F 2240/002* (2013.01); *G06T 2207/20081* (2013.01); *G06T 2207/30068* (2013.01)

(58) Field of Classification Search
CPC ........... G06T 7/337; G06T 2207/20081; G06T 2207/3006
See application file for complete search history.

(56) References Cited

U.S. PATENT DOCUMENTS

| | | | | |
|---|---|---|---|---|
| 2014/0023254 | A1* | 1/2014 | Ishikawa | G06T 7/0012 382/131 |
| 2019/0236783 | A1* | 8/2019 | Ichinose | G06T 7/0016 |
| 2020/0178936 | A1* | 6/2020 | Padwal | A61B 5/4312 |

OTHER PUBLICATIONS

International Search Report issued in PCT/KR2020/018592; mailed Apr. 7, 2021.

Jeong, Young-Jin et al., "Development of segmentation/modeling algorithm using medical imaging (MRI) and 3D scanning data for 3D printing artificial implants for breast reconstruction in breast defects," published Dec. 2018.

Wang, L. et al., "Breast-Shape Classification and Implant Construction Method for Unilateral Breast Reconstruction", published Oct. 16, 2019.

* cited by examiner

METHOD AND PROGRAM FOR MODELING PERSONALIZED BREAST IMPLANT

CROSS-REFERENCE TO RELATED APPLICATION

The present application is a continuation of International Patent Application No. PCT/KR2020/018592, filed on Dec. 17, 2020, which is based upon and claims the benefit of priority to Korean Patent Application No. 10-2019-0171953, filed on Dec. 20, 2019 and Korean Patent Application No. 10-2020-0176976, filed on Dec. 17, 2020. The disclosures of the above-listed applications are hereby incorporated by reference herein in their entirety.

BACKGROUND

1. Technical Field

The present disclosure relates to a method, a program and a system for modeling a personalized breast implant.

2. Description of Related Art

In general, an artificial breast implant is used for breast reconstruction with respect to breast defects due to accidents or diseases, such as breast cancer, or in plastic surgery for beauty or for changing deformity, and demand for artificial breast implants has increased due to an increase of a breast cancer incidence and survival rate.

However, people have breasts different from each other in shape and size, and both breasts of a person are asymmetrical. So, in a case in which breast reconstruction is performed using a breast implant which is not personalized but is varied only in size, it may be difficult to have an original breast shape and it may cause discomfort.

Moreover, the inner boundary surface of the breast and the boundary surface of the implant coupled to the breast and the shape/volume of the cut breast and the shape/volume of the implant may not match, and thus, formation of an empty space inside the breast, skin perforation due to friction between the implant and soft tissues, and complications, such as seroma or the like may result therefrom.

SUMMARY

The present disclosure has been made to solve the above-mentioned problems occurring in the prior art, and an object in an aspect of the present disclosure is to provide a method for modeling a personalized breast implant by merging medical image data and body scan data of a specific patient.

The aspects of the present disclosure are not limited to those mentioned above, and other aspects not mentioned herein will be clearly understood by those skilled in the art from the following description.

To accomplish the above objects, in an aspect of the present disclosure, there is provided a method for modeling a personalized breast implant including the operations of: obtaining medical image data and body scan data; obtaining first image data by 3D modeling the medical image data; obtaining second image data by 3D modeling the body scan data; creating third image data by merging the first image data and the second image data; and creating breast implant appearance information on the basis of the third image data.

Moreover, the operation of creating the breast implant appearance information is performed by using a machine learning model, and learning data for the machine learning model is comprised of the medical image data, the first image data, the body scan data, the second image data, and the third image data.

Furthermore, the merging is performed through image registration, and the image registration includes at least one among feature element registration and template-based registration.

Additionally, the third image data is created in a different manner with respect to the left breast and the right breast.

In addition, the first image data includes information on breast muscles, and the second image data includes information on shape, size and volume of the breast.

In another aspect of the present disclosure, provided is a breast implant modeling system including: a medical image obtaining unit obtaining medical image data; a body image obtaining unit obtaining body scan data; and a processor obtaining first image data by 3D modeling the medical image data, obtaining second image data by 3D modeling the body scan data, creating third image data by merging the first image data and the second image data, and creating breast implant appearance information on the basis of the third image data.

Other detailed matters of the present disclosure are contained in the detailed description and drawings.

DETAILED DESCRIPTION

Figure 1:
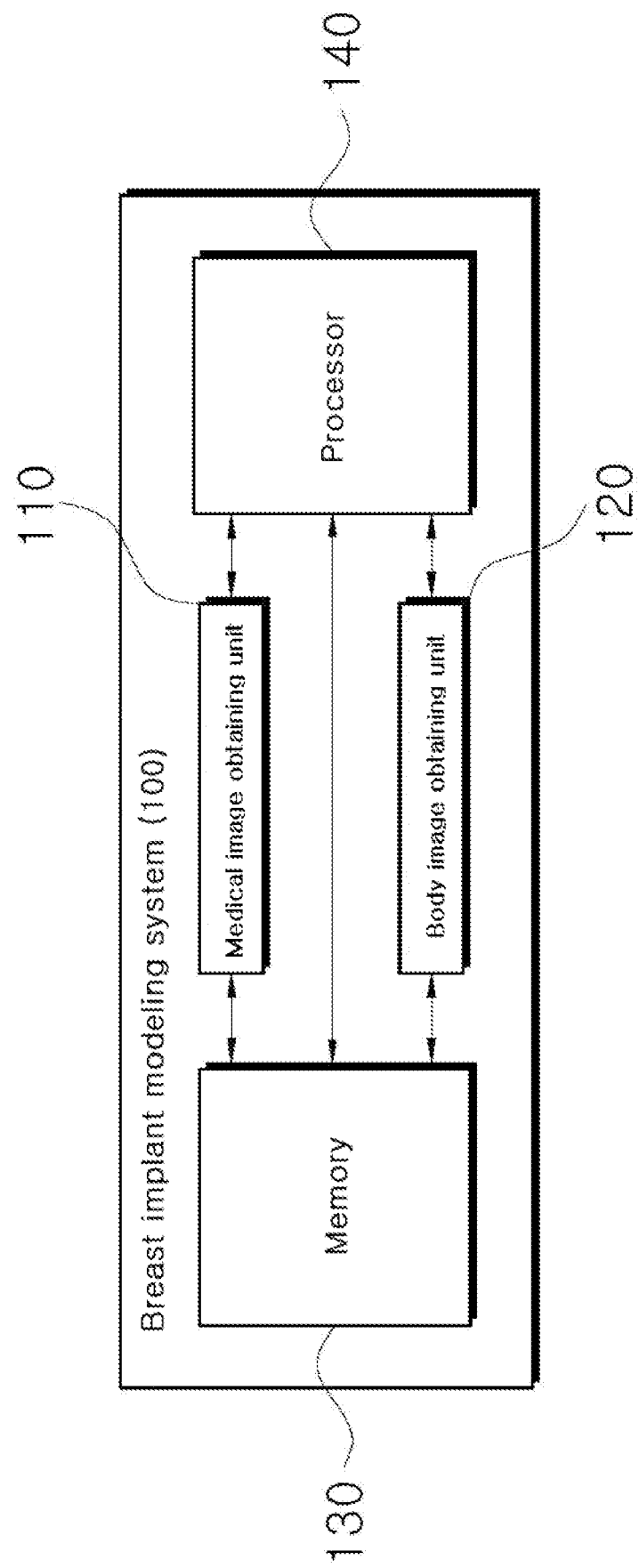
FIG. 1 is a block diagram of a breast implant modeling system according to an embodiment of the present disclosure.

Advantages and features of the present disclosure and methods accomplishing the advantages and features will become apparent from the following detailed description of exemplary embodiments with reference to the accompanying drawings. However, the present disclosure is not limited to exemplary embodiment disclosed herein but will be implemented in various forms. The exemplary embodiments are provided so that the present disclosure is completely disclosed, and a person of ordinary skilled in the art could fully understand the scope of the present disclosure. Therefore, the present disclosure will be defined only by the scope of the appended claims.

Terms used in the specification are used to describe specific embodiments of the present disclosure and are not intended to limit the scope of the present disclosure. In the specification, terms having a singular form may include plural forms unless otherwise specified. It should be also understood that the terms of 'include' or 'have' in the specification are used to mean that there is no intent to exclude existence or addition of other components besides components described in the specification. In the detailed description, the same reference numbers of the drawings refer to the same or equivalent parts of the present disclosure, and the term "and/or" is understood to include a combination of one or more of components described above. It will be understood that terms, such as "first" or "second" may be used in the specification to describe various components but are not restricted to the above terms. The terms may be used to discriminate one component from another component. Therefore, of course, the first component may be named as the second component within the scope of the present disclosure.

The term "exemplary" is used herein as the meaning of "used as an example or an illustration." It should be understood that any of the embodiments described herein as "exemplary" should not necessarily be construed as being preferred or having advantages over other embodiments.

The term, "unit," used in the present disclosure means a hardware element, such as software, FPGA, or ASIC, and the "unit" performs some roles. However, the term, "unit," is not limited to software or hardware. The "unit" may be configured in an addressable storage medium or may be configured to play one or more processors. Therefore, as an example, a "unit" includes elements, such as software elements, object-oriented software elements, class elements, and task elements, processes, functions, attributes, procedures, subroutines, segments of program codes, drivers, firmware, microcode, circuits, data, databases, data structures, tables, arrays, and variables. Functions provided within the elements and "units" may be combined with a smaller number of elements and "units" or may be further divided into additional elements and "units."

In addition, all "units" in the present disclosure may be controlled by at least one processor, and the at least one processor may perform the operation performed by the "unit" of the present disclosure.

Embodiments of the present disclosure may be described in terms of a function or a block performing the function. A block which may be referred to as a "unit" or a "module" of the present disclosure can be physically implemented by an analog or digital circuit, such as a logic gate, an integrated circuit, a microprocessor, a microcontroller, a memory, a passive electronic component, an active electronic component, an optical component, or hardwired circuits, etc., and may be selectively operated by firmware and software.

Embodiments according to the present disclosure can be implemented using at least one software program executed on at least one hardware device, and can perform a network management function to control elements.

Terms, such as "below," "beneath," "lower," "above," "upper," and the like, which have spatially relative concepts, may be used to facilitate correlation between one component and other components, as illustrated in the drawings. Such spatially relative terms should be understood as terms including different directions of components during use or operation, in addition to the direction illustrated in the drawings. For example, if the components illustrated in the drawings are turned upside down, the components described as "below" or "beneath" may be placed "above" of other components. Thus, the exemplary term "under" may include all of the directions, "below" and "above." The components may be oriented in other directions, so that the spatially relative terms can be interpreted according to the orientation.

Unless otherwise defined, all terms (including technical and scientific terms) used herein have the same meaning as commonly understood by those skilled in the technical field to which the present disclosure pertains. It will be further understood that terms, such as those defined in commonly used dictionaries, should not be interpreted in an idealized or overly formal sense unless expressly so defined herein.

In this specification, "medical image data" includes magnetic resonance imaging (MRI), computerized tomography (CT), positron emission tomography (PET), ultrasonography, or mammography, but is not limited thereto, and includes all image data capturing a patient's body for medical purposes.

In this specification, 'body scan data' includes all pieces of image data scanning the exterior of the body of a patient.

In this specification, 'first image data' is image data obtaining a muscle region from the medical image data of a 3D modeled breast region.

In this specification, 'second image data' is image data three-dimensionally modeling a breast region of the body scan data.

In this specification, 'third image data' is image data merging the first image data and the second image data.

Hereinafter, preferred embodiments of the present disclosure will be described in detail with reference to the accompanying drawings.

FIG. 1 is a block diagram of a breast implant modeling system according to an embodiment of the present disclosure.

According to an embodiment of the present disclosure, the breast implant modeling system 100 includes a medical image obtaining unit 110, a body image obtaining unit 120, a memory 130, and a processor 140.

The breast implant modeling system 100 may include all kinds of electronic devices capable of installing and executing an application related to an embodiment of the present disclosure, and may be one of electronic devices, such as a computer, an ultra-mobile PC (UMPC), a workstation, a netbook, a personal digital assistant (PDA), a portable computer, a web tablet, a wireless phone, a mobile phone, a smart phone, and a portable multimedia player (PMP). The electronic device may perform all kinds of services, such as configuration of a service screen, data input, data transmission/reception, data storage, etc., under control of an application.

The breast implant modeling system 100 can obtain medical image data through the medical image obtaining unit 110. Here, the medical image data may include an MRI image or a CT panoramic image.

Moreover, the breast implant modeling system 100 can obtain body scan data scanning a body through the body image obtaining unit 120. Here, the body scan data can include all kinds of image data gathered from scanning the exterior of the body of a patient.

The memory 130 according to the present disclosure is a local storage medium capable of storing first image data, second image data, and third image data extracted by the medical image data, the body scan data, and the processor 140. If necessary, the processor 140 may use the data stored in the memory 130. In addition, the memory 130 according to the present disclosure may store instructions, or the likes for operating the processor 140.

In addition, the memory 130 according to the present disclosure may be provided with a writable non-volatile memory capable of saving data even if power supplied to the personalized breast implant modeling system is cut off and reflecting changes. That is, the memory 130 may be any one of a flash memory, an EPROM, and an EEPROM. For convenience of description, it is described that all instruction information is stored in one memory 130, but the present disclosure is not limited thereto. The breast implant modeling system 100 may include a plurality of memories.

According to an embodiment of the present disclosure, the processor 140 three-dimensionally models the medical image data, divides a muscle region from the 3D image data to obtain or extract first image data. In one embodiment, the muscle region may include the muscle region combined with a breast region containing the mammary gland or fat.

In addition, the processor 140 can three-dimensionally model the body scan data to obtain second image data. In this case, the second image data obtained by the processor 140 is obtained by three-dimensionally modeling the image data scanned from a patient's erect posture, and can include a breast region among parts of the body. Accordingly, the second image data may include the overall shape, size, volume, and the like of the breast.

According to an embodiment of the present disclosure, in a case in which the body scan data is data obtained by 3D scanning, additional 3D modeling process can be omitted.

When the first image data and the second image data are obtained, the processor 140 can merge the first image data and the second image data to obtain third image data. In this case, the third image data may be data including the overall shape, size, volume and the like of the breast region and the muscle region combined with the breast region including the mammary gland or fat.

When the third image data is obtained, the processor 140 can create breast implant appearance information based on the third image data.

In the present specification, it is described that the processor obtains the first image data and the second image data, but the present disclosure is not limited thereto. In one embodiment, the first image data is obtained from the medical image obtaining unit 110 and the second image data is obtained from the body image obtaining unit 120 so that the processor 140 may obtain third data by merging the first image data and the second image data to model a personalized breast implant.

Figure 2:
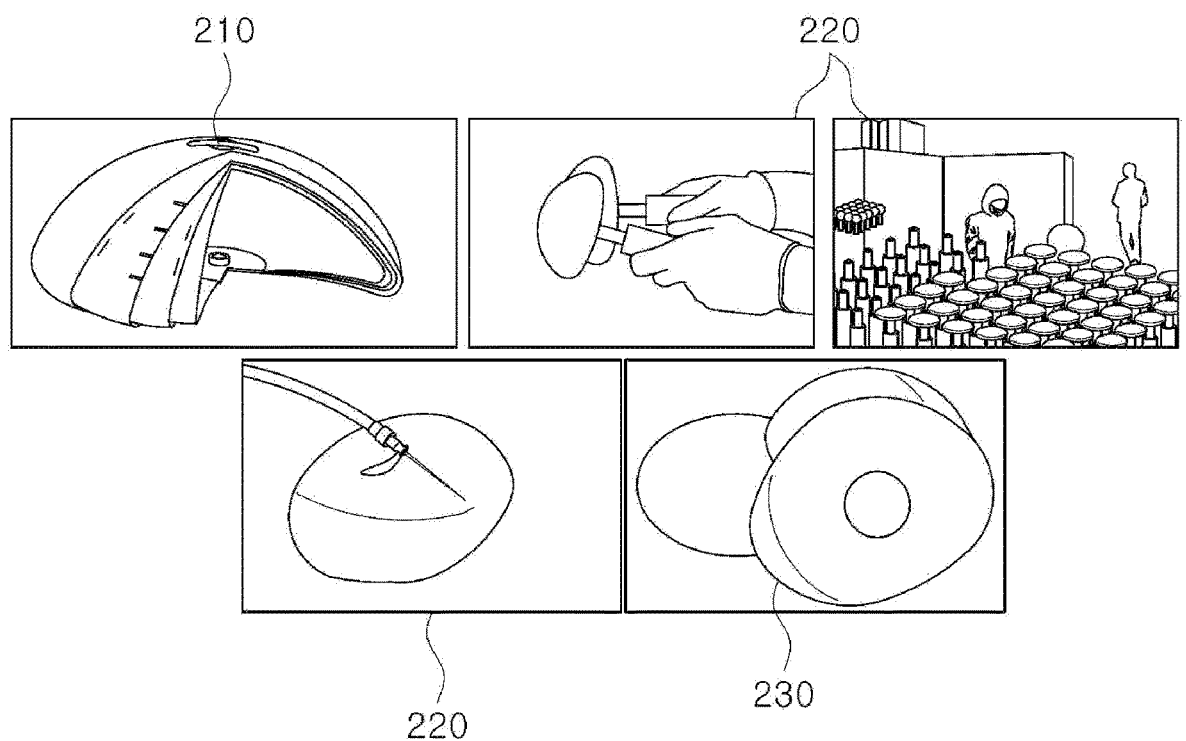
FIG. 2 is a schematic view illustrating manufacturing of a breast implant according to an embodiment of the present disclosure.

FIG. 2 is a schematic view illustrating manufacturing of a breast implant according to an embodiment of the present disclosure.

As illustrated in FIG. 2, according to embodiments of the present disclosure, a personalized breast implant like a breast implant 210 can be manufactured.

In a case in which the processor 140 creates breast implant appearance information based on the third image data, the personalized breast implant 230 can be manufactured through the manufacturing process 220.

Figure 3:
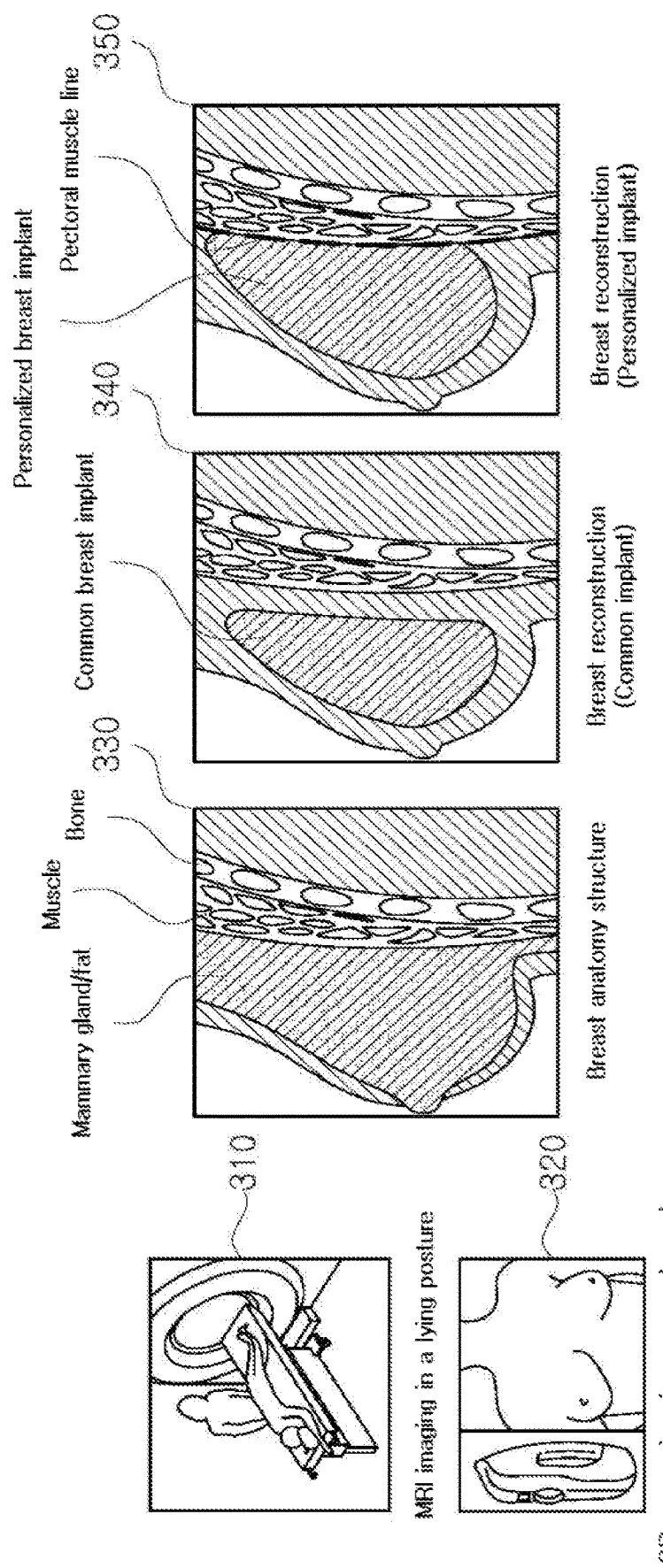
FIG. 3 is a schematic view illustrating a breast implant modeling process according to an embodiment of the present disclosure.

FIG. 3 is a schematic view illustrating a breast implant modeling process according to an embodiment of the present disclosure.

In general, in a case of a patient requiring a breast implant, a medical image photographing including MRI is performed. In the same way, in the case of a patient who has received breast cancer diagnosis, medical imaging is performed in order to precisely check a range of lesion and to make a surgery plan. In this case, the MRI is performed in a lying posture illustrated in a picture 310, which is difficult to confirm the breast appearance in ordinary situations, for example, a situation in which a patient is standing.

In other words, when the electronic device such as the breast implant modeling device 100 performs 3D modeling for producing a breast implant on the basis of only medical image data including MRI, it is easy to secure a patient's image data including information on the inside of the breast, such as breast muscles. However, since most medical image data is obtained in a state in which a patient lies, it is difficult to reproduce the breast in ordinary situations. Therefore, in order to manufacture a personalized breast implant, additional photographing must be performed several times, and it causes lots of photographing time and expenses.

Alternatively, as shown in picture 320, in a case in which an implant is modeled based on only the body scan data, it is easy to rapidly photograph the body in an erect posture and it is also easy to reproduce the breast in ordinary situations, but breast internal information cannot be obtained. For instance, the entire shape, size, volume, and the like of the breast can be seen through the body scan data, but it is difficult to produce a personalized breast implant since the position and structure of the internal muscles are not found through the body scan data.

As shown in picture 330, the breast in the woman's body comprises the mammary gland or fat covering the bones and muscles, and is comprised of the outermost skin of the body. People are varied in shape, size, or internal structure of the breast. In addition, people have right breasts and left breasts different from each other in shape, size, or internal structure. Embodiments of the present disclosure can provide a personalized breast implant for the appearance of the breast of each person.

A picture 340 illustrates a state in which a general common breast implant is inserted. As shown in the picture 340, the common breast implant cannot reflect a muscle region such as the pectoral muscle line, to the breast implant well, and cannot reflect the appearance of the breast well. So, the common breast implant cannot provide an implant suitable for a patient's breast.

The present disclosure can provide a personalized breast implant such as shown in a picture 350 in consideration of the muscle region combined with the breast region including the mammary gland or fat and the whole shape, size, volume, and the like of the breast by merging the first image data and the second image data.

Figure 4:
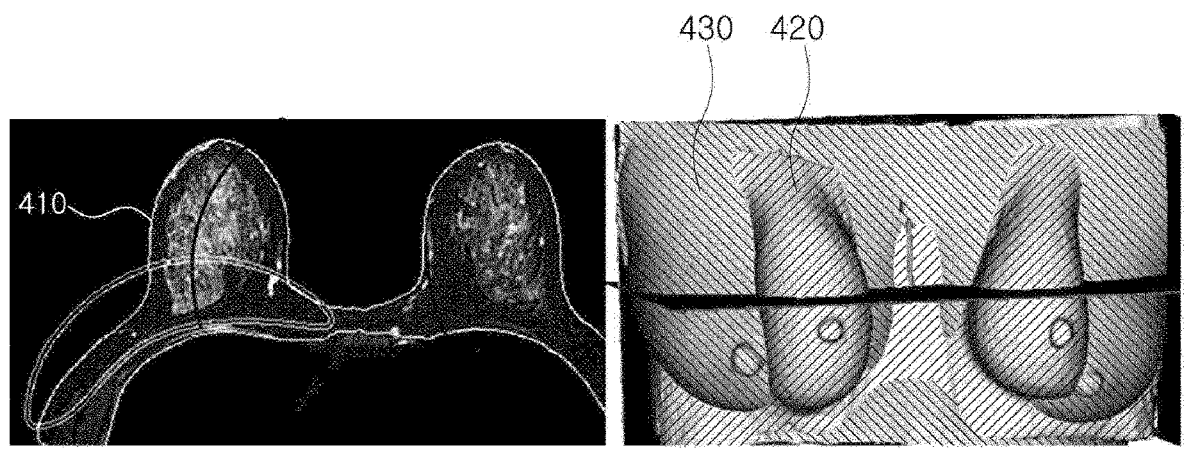
FIG. 4 is a schematic view illustrating a breast implant modeling process according to an embodiment of the present disclosure.

FIG. 4 is a schematic view illustrating a breast implant modeling process according to an embodiment of the present disclosure.

An MRI image 410 may include an appearance of the breast, an internal muscle region, and the mammary gland or fat. In this case, since the MRI image 410 is generally imaged in a lying posture, a 3D modeling image 420 based on the MRI image 410 cannot accurately reflect the appearance of the breast, as shown. On the other hand, since body scanning is performed in an erect posture, the 3D modeling image 420 based on the body scan data can reflect the appearance of the breast in an ordinary environment. Therefore, as described above, a process of merging the first image data obtained from the medical image data and the second image data obtained by 3D modeling the breast region of the body scan data is required.

Figure 5:
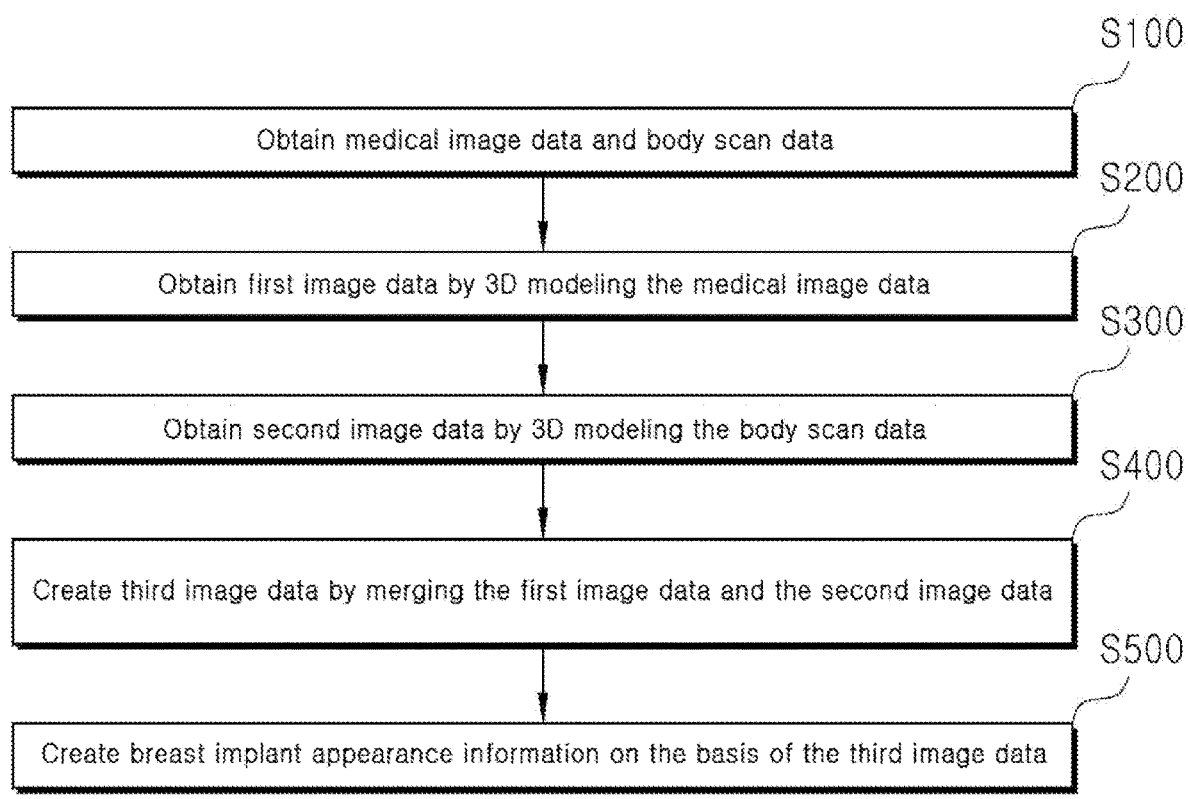
FIG. 5 is a flow chart illustrating a breast implant modeling process according to an embodiment of the present disclosure.

FIG. 5 is a flow chart illustrating a breast implant modeling process according to an embodiment of the present disclosure.

Each of the operations of the breast implant modeling method according to the present disclosure can be performed by various types of electronic devices including a medical image obtaining unit 110, a body image obtaining unit 120, a memory 130, and a processor 140.

Hereinafter, with reference to FIG. 5, a process of modeling a personalized breast implant according to the present disclosure will be described in detail.

The embodiments described with respect to the breast implant modeling system 100 are applicable to at least some or all of the breast implant modeling method, and the embodiments described with respect to the breast implant modeling method are applicable to at least some or all of the embodiments for the breast implant modeling system. In addition, the breast implant modeling method according to the disclosed embodiments is performed by the breast implant modeling system 100 disclosed in the present specification, and the embodiments are not limited thereto, and can be performed by various types of electronic devices.

First, the processor 140 can obtain medical image data and body scan data through the medical image obtaining unit 110 and the body image obtaining unit 120 (S100).

The medical image data may include an MRI image or a CT image. In addition, the body scan data may include all pieces of image data obtained by scanning the exterior of the body of a patient.

Next, the processor 140 can three-dimensionally model the medical image data, and segment the muscle region from the 3D image data to obtain (or extract) the first image data (S200).

According to an embodiment of the present disclosure, the processor 140 can perform 3D modeling by segmenting the breast region from medical image data of a patient, and segment the muscle region from the modeled 3D image data. According to the present disclosure, the segmentation or the 3D modeling method is not limited.

Next, the processor 140 can 3D model the body scan data and obtain second image data (S300).

In one embodiment, the second image data may mean a breast region of the body scan data. Furthermore, in a case in which the body scan data is data obtained by 3D scanning, additional 3D modeling process can be omitted.

Next, the processor 140 can create third image data by merging the first image data and the second image data (S400).

The process of merging the first image data and the second image data will be described in detail with reference to FIG. 8.

Next, the processor 140 can create breast implant appearance information based on the third image data (S500).

In this case, since the first image data includes information on the muscle inside the breast and the second image data includes information on the shape, size, volume, and the like, the processor 140 can perform modeling of a personalized breast implant sample touching muscles, in detail, the pectoral muscle line, and corresponding to the shape of the breast, such as the picture 350.

Figure 6:
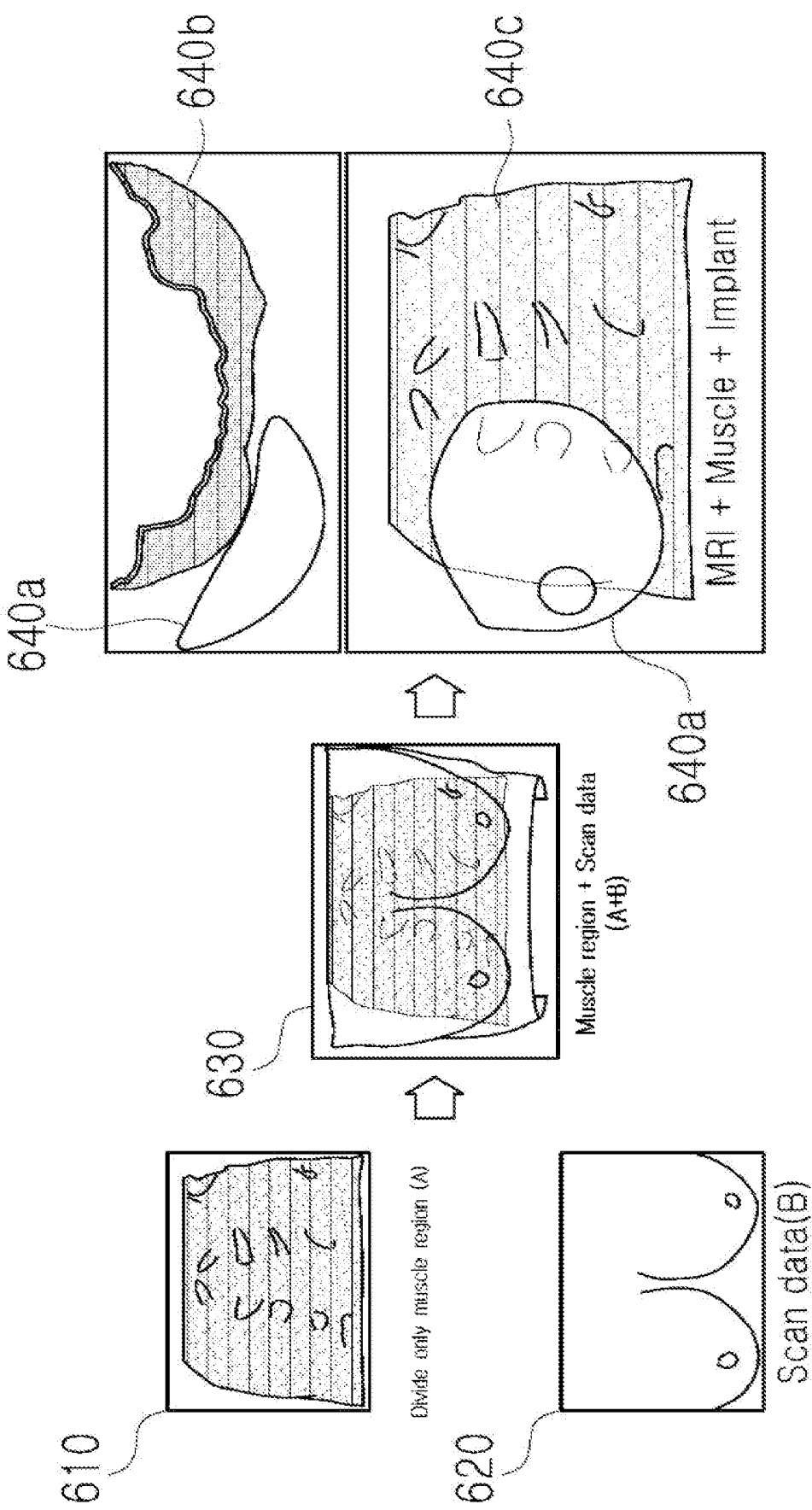
FIG. 6 is a schematic view illustrating a breast implant modeling process according to an embodiment of the present disclosure.

FIG. 6 is a schematic view illustrating a breast implant modeling process according to an embodiment of the present disclosure.

As described in operation S200 of FIG. 5, the processor 140 can obtain the first image data by performing 3D modeling of the medical image data and segmenting the muscle region 610 from the 3D image data to obtain first image data. In one embodiment, the muscle region 610 may include the pectoral muscle line inside the breast. Additionally, the breast implant modeled according to embodiments of the present disclosure can get in contact with the muscle region 610. Accordingly, a patient can be provided with a breast implant accurately matching the breast muscle boundary surface.

Moreover, as described in operation S300 of FIG. 5, the processor 140 can 3D model the body scan data and obtain second image data for the breast area 620. In one embodiment, the breast region (620) is obtained through body scanning, and the second image data can include information about the shape, size and volume of the breast.

As described in operation S400 of FIG. 5, the processor 140 may merge the first image data and the second image data to generate third image data, such as the picture 630.

In addition, as described in operation S500 of FIG. 5, the processor 140 may generate breast implant appearance information based on the third image data. A personalized breast implant 640a can be provided to a patient based on the generated appearance information. As illustrated in FIG. 6, the breast implant can be in contact with the breast muscles 640b and 640c in the breast.

Figure 7:
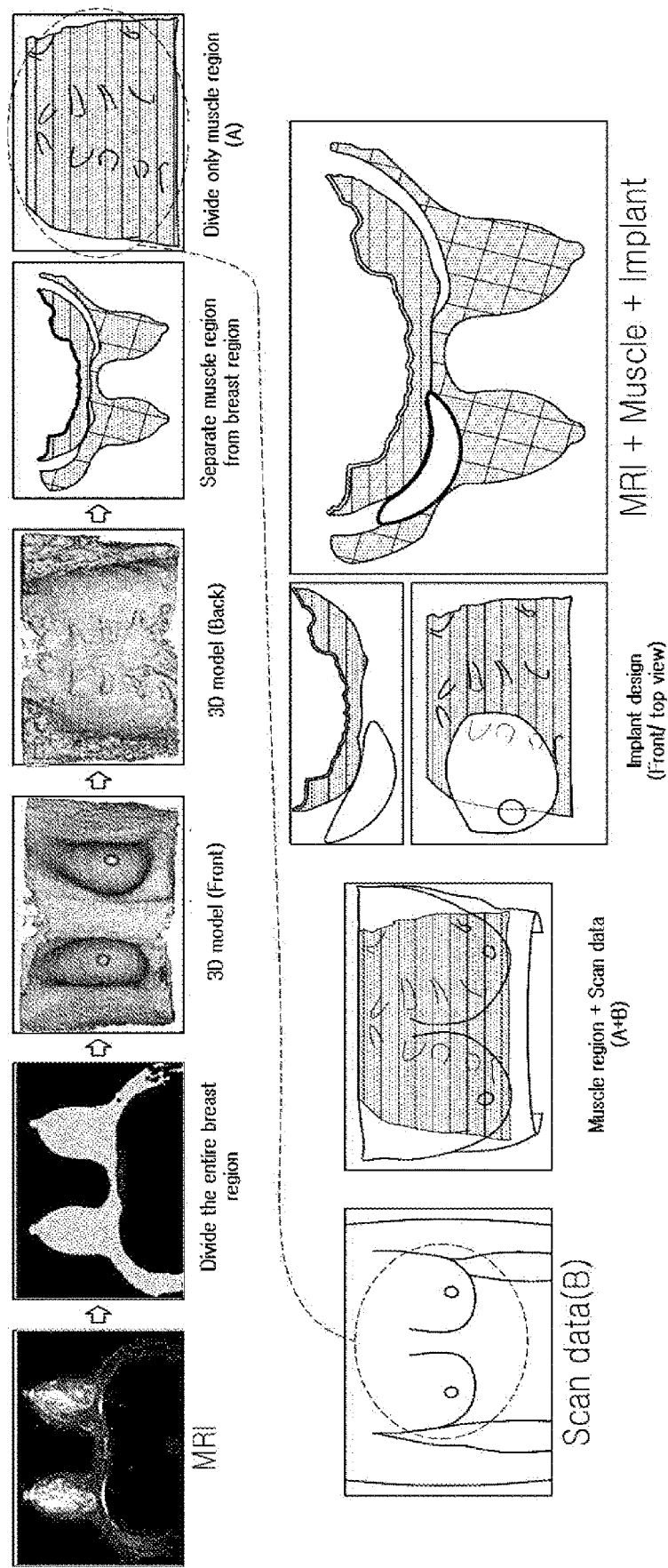
FIG. 7 is a schematic view illustrating a breast implant modeling process according to an embodiment of the present disclosure.

FIG. 7 is a schematic view illustrating a breast implant modeling process according to an embodiment of the present disclosure.

A series of the process illustrated in FIG. 7 is to visually illustrate the breast implant modeling process of FIG. 5, and so, a detailed description thereof will be omitted.

Figure 8:
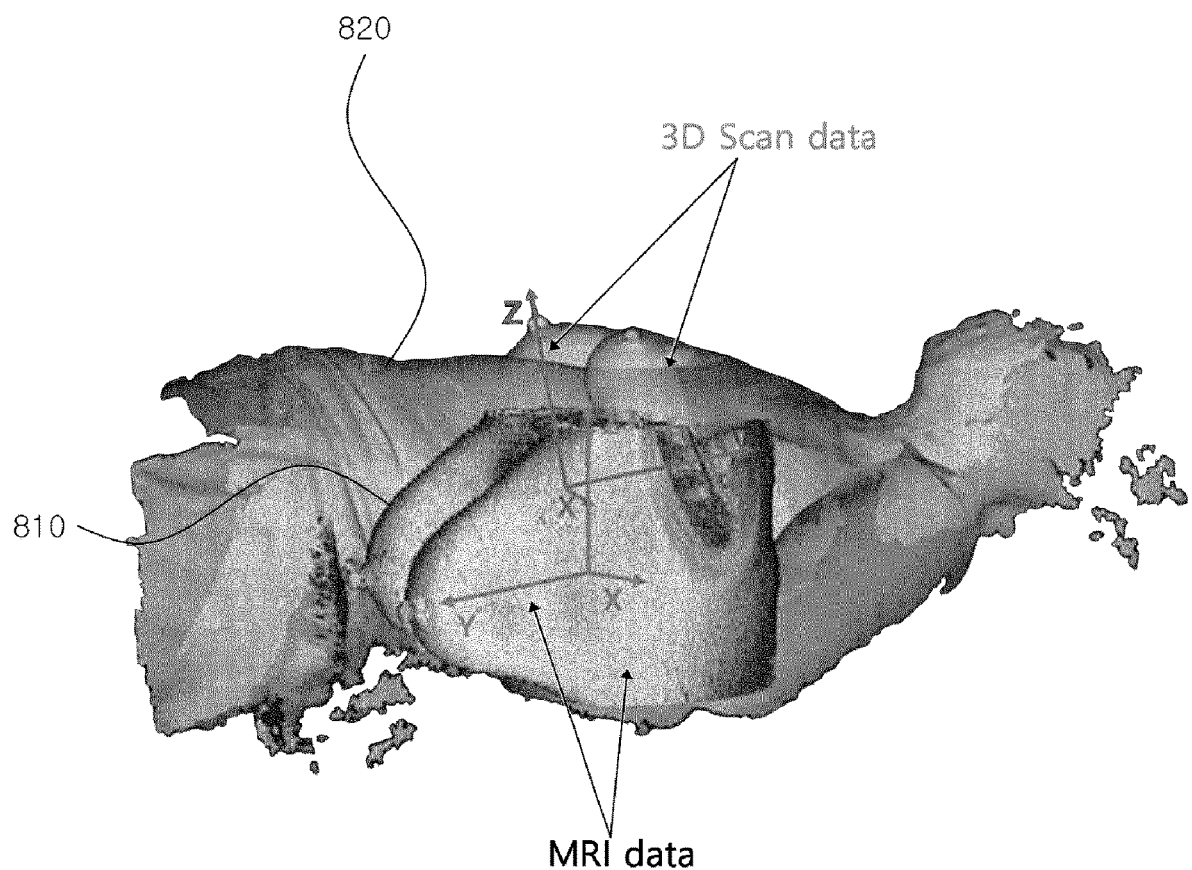
FIG. 8 is a schematic view illustrating a breast implant modeling process according to an embodiment of the present disclosure.

FIG. 8 is a schematic view illustrating a breast implant modeling process according to an embodiment of the present disclosure.

The processor 140 merges first image data and second image data to generate third image data. Specifically, the processor 140 may generate third image data through image registration.

The image registration means technology for obtaining a cross-sectional shape of a region of interest from image contents obtained by different imaging devices and moving and superimposing the same to one reference coordinate.

According to an embodiment of the present disclosure, the image registration may include feature element matching of extracting and registering important features of an image or template-based registration of comparing a certain region in the image with a designated template and distinguishing an area having the highest similarity.

The feature element registration may have four stages of feature extraction, feature matching between feature elements, transformation model estimation, and image registration.

Furthermore, the feature matching includes an intensity-based matching method, such as cross-correlation (CC), mutual information (MI), least-squares matching (LSM), or the like, and a feature-based matching method, such as scale-invariant feature transform (SIFT), speeded up robust features (SURF), or the like.

According to an embodiment of the present disclosure, in a case in which the feature-based matching method is used for the image registration, axes of first image data 810 and second image data 820 are aligned. In one embodiment, the axis of the image data refers to X, Y, and Z axes in a three-dimensional space.

In addition, the size and position of each image can be adjusted by extracting and matching a plurality of feature points from the first image data 810 and the second image data 820. In one embodiment, the feature point includes a specific point in which the position in the three-dimensional space does not change according to a patient's condition change, for instance, breathing.

In one embodiment, the feature extraction may be implemented by an artificial intelligence algorithm including machine learning or deep learning.

When the plurality of feature points are extracted, the sizes and locations of the first image data 810 and the second image data 820 are matched and merged based on the distances or locations between the plurality of feature points to generate third image data.

Figure 9:
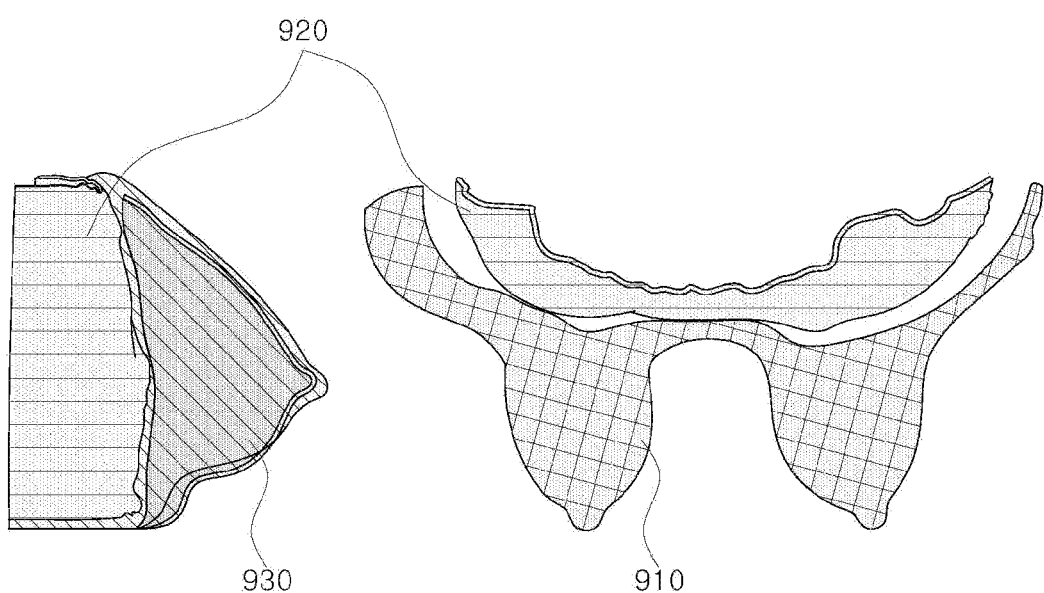
FIG. 9 is a schematic view illustrating a breast implant modeling process according to an embodiment of the present disclosure.

FIG. 9 is a schematic view illustrating a breast implant modeling process according to an embodiment of the present disclosure.

The breast includes a first breast region 910 mainly consisting of the mammary gland and fat, and a second breast region 920 consisting of the pectoral muscle. In a case in which a medical image, for example, MRI is captured in a state in which a patient lies down, the shape of the first breast region 910 varies greatly according to the patient's posture but the shape of the second breast region 920 does not vary greatly according to the patient's posture, namely, according to an erect posture and a lying posture. Therefore, a portion coming in contact with the muscle region in the implant can be modeled by using information contained in the first image data. In addition, modeling of the size and shape of the implant can be performed by using information contained in the second image data 930 obtained from the body scan data.

Figure 10:
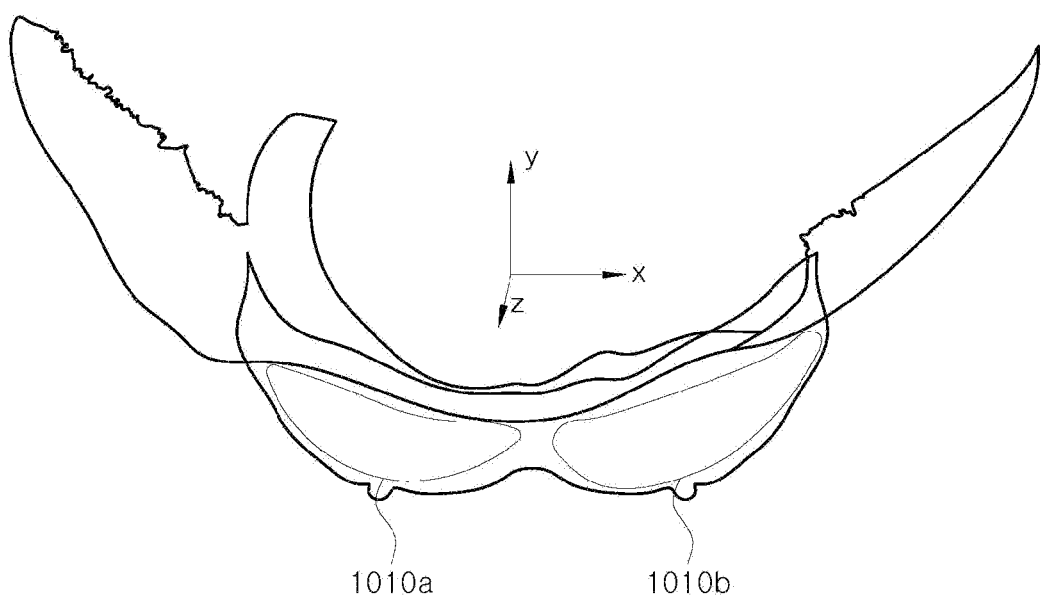
FIG. 10 is a schematic view illustrating a breast implant according to an embodiment of the present disclosure.

FIG. 10 is a schematic view illustrating a breast implant according to an embodiment of the present disclosure.

A person may have a left breast and a right breast different from each other in terms of shape, size, or internal structure. According to embodiments disclosed in the present disclosure, both of a right breast implant 1010a and a left breast implant 1010b can be modeled. Accordingly, a patient can be provided with personalized breast implants. Therefore, since the breast implants may exactly match the patient's breast muscle boundary surface and have volume equal to that of the patient's breasts, the present disclosure provides an effect of minimizing skin perforation due to friction between the implant and the cut section of the breast and complications, such as seroma or the like.

In the present disclosure, various embodiments through the processor 130 may be implemented using a machine learning model. As an example, a deep neural network (DNN) of the present disclosure may include a system or network for constructing one or more layers in one or more computers to perform determination based on a plurality of pieces of data.

The deep neural network may be implemented as a set of layers including a convolutional pooling layer, a locally-connected layer, and a fully-connected layer.

The convolutional pooling layer or the locally-connection layer may be configured to extract features in the image.

The fully-connected layer may determine a correlation between features of the image.

As another example, the overall structure of the deep neural network of the present disclosure may be formed in a form in which the locally-connection layer is connected to the convolutional pooling layer and the fully-connected layer is connected to the locally-connection layer. The deep neural network may include various determination criteria, namely, parameters, and may add new decision criteria, namely, parameters, through input image analysis.

The deep neural network according to embodiments of the present disclosure is a convolutional neural network suitable for image analysis, and has a structure in which a feature extraction layer of learning features with the greatest discriminative power from given image data on its own and a prediction layer of learning a prediction model to show the height prediction performance based on the extracted features are integrated.

The feature extraction layer may be formed in a structure in which the convolutional layer making a feature map by applying a plurality of filters to each region of the image and a pooling layer capable of extracting features immutable to changes in location or rotation by spatially integrating the feature map are repeated several times in turn. So, features of various levels ranging from features of a low level, such as a dot, a line, a side, and the like, to features of a high level which is complicated and meaningful can be extracted.

The convolutional layer takes a non-linear activation function to an inner product of a local receptive field and a filter for each patch of the input image to obtain a feature map. Compared with another network structure, CNN uses a filter having sparse connectivity and shared weights. Such a connection structure reduces the number of parameters to be learned and provides effective learning through a back-propagation algorithm to finally enhance prediction performance.

The pooling layer or sub-sampling layer generates a new feature map using the local information of the feature map obtained from the previous convolutional layer. In general, the feature map newly created by the integrated layer is reduced to a size smaller than that of the original feature map, and a representative integration method includes maximum pooling selecting a maximum value of the corresponding area in the feature map, and average pooling obtaining an average value of the corresponding area in the feature map. The feature map of the pooling layer may be less affected by the location of any structure or pattern existing in the input image than the feature map of the previous layer. That is, the pooling layer can extract features robust to local changes, such as noise or distortion, in the input image or the previous feature map, and this feature can play an important role in classification performance. The role of another pooling layer is to reflect features of a wider region as ascending to a learning layer of a higher level in the deep structure. As the feature extraction layer are stacked, a lower layer reflects local features, and an upper layer reflects features of the overall abstract image as ascending toward upper layers.

As described above, the classification model, such as multilayer perception (MLP) or a support vector machine (SVM), can be connected in the form of a fully-connected layer to be used for classification model learning and prediction.

Moreover, according to one embodiment of the present disclosure, the learning data for machine learning may be generated based on a U-Net-dhSegment model. Here, the U-Net-dhSegment model sets an expansive path to be symmetric with a contracting path based on fully convolutional networks (FCNs) of end-to-end to generate a U-shaped architecture having skip connection for each level.

Additionally, the learning data for the machine learning model may include medical image data, first image data, body scan data, second image data, and third image data.

Accordingly, the processor 140 can perform a personalized breast implant modeling process described above in FIGS. 5 and 8 by using the machine learning model learned through the learning data.

The present disclosure can perform modeling of a personalized breast implant by obtaining 3D image information of a breast muscle region of a patient by utilizing existing medical image data without additional medical image photographing to manufacture personalized breast implant for the patient, and creating and merging 3D image information on the breast appearance of the patient through simple 3D scanning in an erect posture.

Furthermore, according to the personalized breast implant modeled according to the present disclosure, it is possible to reproduce a breast appearance in an ordinary situation of a patient before surgery even after surgery, and the personalized breast implant exactly matches the breast muscle boundary surface of a specific patient and has volume equal to that of the patient's breast, thereby minimizing skin perforation due to friction between the implant and the cut section of the breast and complications, such as seroma or the like.

Various embodiments of the present disclosure may be implemented as software including one or more instructions stored in a storage medium, for instance, a memory, readable by a machine, such as a personalized breast implant modeling system 100, or a computer. For example, a processor of an apparatus, for instance, the processor 140, can call one or more commands among one or more instructions stored in the storage medium, and execute it. This enables the apparatus to perform at least one function in accordance with the one or more instructions called. The one or more instructions may include a code generated by a compiler or a code that may be executed by an interpreter. The machine-readable storage medium may be provided in the form of a non-transitory storage medium. Here, the term "non-transitory storage medium" is a tangible device and does not include a signal, for example, electromagnetic wave, and the term does not distinguish a case in which data is stored semi-permanently in the storage medium and a case in which data is stored temporarily in the storage medium. For example, the non-transitory storage medium may include a buffer in which data is temporarily stored.

According to one embodiment, the method according to various embodiments disclosed herein may be included in a computer program product. The computer program product may be transacted between a seller and a buyer. The computer program product may be distributed in the form of a machine-readable storage medium, for instance, a compact disc read only memory (CD-ROM)), or may be distributed, for example, downloaded or uploaded, through an application store, such as Play Store™, or directly between two user devices, such as smart phones, online. In a case of online distribution, at least a portion of computer program products, for instance, downloadable apps, is temporarily stored or temporarily generated in a machine-readable storage medium, such as a memory of a server of a manufacturer, a server of an application store, or a relay server.

The above description is only exemplary, and it will be understood by those skilled in the art that the disclosure may be embodied in other concrete forms without changing the technological scope and essential features. Therefore, the above-described embodiments should be considered only as examples in all aspects and not for purposes of limitation.

The invention claimed is:

1. A personalized breast implant modeling method performed in a computer comprising:
obtaining medical image data and body scan data;
obtaining first image data by 3D modeling the medical image data, wherein the first image data include information on a breast muscle region, and wherein the information on the breast muscle region includes information on a pectoral muscle line inside a breast, and the first image data are obtained by separating the information on the breast muscle region from the medical image data;
obtaining second image data by 3D modeling the body scan data, wherein the second image data include information on a shape, a size and a volume of the breast;
creating third image data by merging the first image data and the second image data, wherein the merging is performed through an image registration that includes at least one among a feature element registration and a template-based registration; and
creating breast implant appearance information on the basis of the third image data, wherein a personalized breast implant according to the breast implant appearance information is configured to have a portion that gets in contact with the breast muscle region.

2. The method according to claim 1, wherein the creating the breast implant appearance information is performed by using a machine learning model, and
wherein learning data for the machine learning model is comprised of the medical image data, the first image data, the body scan data, the second image data, and the third image data.

3. The method according to claim 1, wherein the merging is performed through the feature element registration, which comprises: aligning axes, which are X, Y, and Z axes in a three-dimensional space, of the first image data and the second image data; adjusting a size and a position of each image of the first image data and the second image data by extracting and matching a plurality of feature points from the first image data and the second image data, wherein the plurality of feature points comprise a specific point in which a position in the three-dimensional space does not change according to a patient's condition change by breathing; and matching sizes and locations of the first image data and the second image data; and merging the first image data and the second image data based on distances or locations between the plurality of feature points.

4. The method according to claim 1, wherein the third image data is created in a different manner with respect to a left breast and a right breast.

5. A non-transitory computer-readable recording medium in which a program for executing the breast implant modeling method according to claim 1 is stored.

6. A breast implant modeling system comprising:
a processor configured to:
obtain medical image data and body scan data;
obtain first image data by 3D modeling the medical image data, wherein the first image data include information on a breast muscle region, and wherein the information on the breast muscle region includes information on a pectoral muscle line inside a breast, and the first image data are obtained by separating the information on the breast muscle region from the medical image data;
obtain second image data by 3D modeling the body scan data, wherein the second image data include information on a shape, a size and a volume of the breast;
create third image data by merging the first image data and the second image data, wherein the merging is performed through an image registration that includes at least one among a feature element registration and a template-based registration; and
create breast implant appearance information on the basis of the third image data, wherein a personalized breast implant according to the breast implant appearance information is configured to have a portion that gets in contact with the breast muscle region.

7. The system according to claim 6, wherein the merging is performed through the feature element registration, which comprises: aligning axes, which are X, Y, and Z axes in a three-dimensional space, of the first image data and the second image data; adjusting a size and a position of each image of the first image data and the second image data by extracting and matching a plurality of feature points from the first image data and the second image data, wherein the plurality of feature points comprise a specific point in which a position in the three-dimensional space does not change according to a patient's condition change by breathing; and matching sizes and locations of the first image data and the second image data; and merging the first image data and the second image data based on distances or locations between the plurality of feature points.

8. The system according to claim 6, wherein the third image data is created in a different manner with respect to a left breast and a right breast.

\* \* \* \* \*